(12) United States Patent
Gallwitz et al.

(10) Patent No.: US 7,678,395 B2
(45) Date of Patent: Mar. 16, 2010

(54) STIMULATION OF HAIR GROWTH BY ISOGINKGETIN

(75) Inventors: Wolfgang E. Gallwitz, San Antonio, TX (US); I. Ross Garrett, San Antonio, TX (US); Gloria Gutierrez, San Antonio, TX (US)

(73) Assignee: Osteoscreen, Inc., San Antonio, TX (US)

( * ) Notice: Subject to any disclaimer, the term of this patent is extended or adjusted under 35 U.S.C. 154(b) by 396 days.

(21) Appl. No.: 10/575,285

(22) PCT Filed: Nov. 2, 2004

(86) PCT No.: PCT/US2004/036502

§ 371 (c)(1),
(2), (4) Date: Apr. 11, 2006

(87) PCT Pub. No.: WO2005/046584

PCT Pub. Date: May 26, 2005

(65) Prior Publication Data

US 2007/0196316 A1   Aug. 23, 2007

Related U.S. Application Data

(60) Provisional application No. 60/517,652, filed on Nov. 5, 2003.

(51) Int. Cl.
*A61K 36/16* (2006.01)
*A61K 36/00* (2006.01)
*A61K 9/00* (2006.01)
*A61K 8/97* (2006.01)

(52) U.S. Cl. .................... 424/752; 424/725; 424/74; 424/400

(58) Field of Classification Search .............. None
See application file for complete search history.

(56) References Cited

U.S. PATENT DOCUMENTS

| 5,965,157 | A | 10/1999 | Li et al. |
|---|---|---|---|
| 6,261,596 | B1 | 7/2001 | Li et al. |
| 6,271,246 | B1 | 8/2001 | Murad |
| 6,410,512 | B1 | 6/2002 | Mundy et al. |
| 6,465,421 | B1 | 10/2002 | Duranton et al. |
| 6,596,266 | B2 | 7/2003 | Catalfo et al. |
| 2004/0076691 | A1 * | 4/2004 | Haines et al. ............... 424/729 |

FOREIGN PATENT DOCUMENTS

| JP | 410287531 A | * 10/1998 |
|---|---|---|
| WO | WO-03/053336 | 7/2003 |

OTHER PUBLICATIONS

Dell'Agli et al., Planta Med. (2002) 68:76-79.
International Search Report for PCT/US04/36502, mailed on May 13, 2005, 2 pages.
Kim et al., Skin Pharmacol. (1997) 10:200-205.
Kobayashi et al., Yakugaku Zasshi (1993) 113:718-724.
Lee et al., Life Sci. (1995) 6:551-558.
Zhonghua Jia et al., J. Nat. Prod. (1998) 11:1368-1373.
Kwak et al., Planta Medica (2002) 68(4):316-321.
Nam et al., The Journal of Biological Chemistry (2001) 276(16):13322-13330.
Supplementary European Search Report for EP 04800621.7, mailed Jun. 2, 2009, 3 pages.

* cited by examiner

*Primary Examiner*—Christopher R Tate
*Assistant Examiner*—Randall Winston
(74) *Attorney, Agent, or Firm*—Morrison & Foerster LLP

(57) ABSTRACT

Flavanoid components of the *Ginkgo biloba* tree are useful to stimulate the growth of hair and are thus useful in treatment of alopecia or baldness.

5 Claims, 4 Drawing Sheets

2-{3-[2,4-Dihydroxy-7-(4-methoxy-phenyl)-5-oxo-5,
8-dihydro-napthalen-1-yl]-4-methoxy-phenyl}
-5,7-dihydroxy-chromen-4-one Effect of 10.0% Isoginkgeting on Hair
Day 17

10.0% Isoginkgetin 1.0% OSA

Vehicle

Effect of 10.0% Isoginkgeting on Hair Day 26

US 7,678,395 B2

STIMULATION OF HAIR GROWTH BY ISOGINKGETIN

CROSS-REFERENCE TO RELATED APPLICATION

This application is the national phase of PCT application PCT/US2004/036502 having an international filing date of 2 Nov. 2004, which claims priority from U.S. provisional application Ser. No. 60/517,652 filed 5 Nov. 2003. The contents of these documents are incorporated herein by reference.

TECHNICAL FIELD

The invention relates both to pharmacology and cosmetology. More specifically, it relates to stimulating hair growth by applying or administering flavanoid-enriched extracts of *Ginkgo biloba*.

BACKGROUND ART

Extracts of leaves and seeds of *Ginkgo biloba* have been used for many years, originally in China, and now throughout the world, to exert various physiological effects. The seeds of *Ginkgo* have been used by the Chinese to treat cancer, respiratory and circulatory problems and impaired hearing; seed extracts have been used to promote sexual desire and enhanced longevity. Extracts obtained from *Ginkgo* leaves have been used in Western cultures for various therapeutic purposes.

A particular extract from leaves, EGb761 (Tebofortan) has been used in clinical trials. On a wt/wt basis, this extract contains 24% of flavone glycosides and 6% terpenoids. Among conditions treated by this and other *Ginkgo* extracts are cerebral insufficiency, inadequate blood circulation, and various heart conditions. The extracts have also been used as scavengers for free radicals.

The physiological basis for the use of *Ginkgo* extracts has been explored in a number of studies on model systems. However, of most relevance to the present invention is a study conducted by Kobayashi, N., et al., published in *Yakugaku Zasshi* (1993) 113:718-724 wherein the above-referenced extract, EGb761, (prepared by extraction of *Ginkgo* leaves in 70% ethanol) was shown to stimulate hair growth in CH3 strain mice when applied topically to a shaved dorsal surface. These workers attributed this stimulatory affect on the ability of the extracts to enhance blood flow. *Ginkgo* extracts were employed in this study based on the postulate that they are known to be effective for chilblains, which is aggravated by poor blood circulation.

A large number of active molecules have been identified in *Ginkgo* leaves, including, most prominently, flavone glycosides and terpenoids. Among the flavone glycosides identified are kaempferol, quercetin, isorhamnetin, sciadopitysin, ginkgetin, amentoflavone, bilobeten, sequoiaflavone and isoginkgetin. The flavone nucleus may be coupled to sugars, including glucose or rhamnose. In particular, the structure of isoginkgetin has been determined and published. It is shown in FIG. 1. The terpenoids include ginkgolides A, B, and C and bilobalide. Ginkgolides are known to inhibit platelet activating factor, thus ginkgolides may be useful in treating asthma, atherosclerosis and stroke when the immune system is stressed and may help restore motor nerves and can also be used to treat certain parasitic infections.

The affects of individual flavanoids derived from *Ginkgo* have also been studied. Saponara, R., et al., *J. Nat. Prod.* (1998) 11:1368-1369 showed that individual *Ginkgo* flavones inhibit the activity of cAMP phosphodiesterase in rat adipose tissue. They also stimulate skin microcirculation. Dell'Agli, M., et al., *Planta Med.* (2002) 68:76-79 showed that various *Ginkgo* flavones stimulated the lipolysis in adiposites in a dose-dependent manner. The individual flavones derived from *Ginkgo* also stimulated human skin fibroblasts and increased production of collagen and extracellular fibronectin, as described by Kim, S. J., et al., *Skin Pharmacol.* (1997) 10:200-205. Some of the flavones also suppressed lymphocyte proliferation as described by Lee, S. J., et al., *Life Sci.* (1995) 6:551-558.

To applicants' knowledge, there is no suggestion that the stimulation of hair growth described by Kobayashi (supra) was attributable to the flavanoid components of *Ginkgo*.

U.S. Pat. No. 6,410,512 describes the effect of proteasome inhibitors on hair growth. It appears that inhibition of proteasome activity and/or NF-κB activity results in enhanced hair growth. Applicants are aware of no publication or description in the art that associates *Ginkgo* flavanoids with proteasome inhibition.

DISCLOSURE OF THE INVENTION

It has been found that the flavanoid fraction of an extract of *Ginkgo* leaves, and in particular the individual flavanoid components, are effective in stimulating the growth of hair in hair-bearing animals. Individual flavanoids can be used either topically or systemically to effect hair growth or extracts enriched in flavanoid content may be employed. The individual flavanoids or mixtures thereof may be prepared synthetically where such preparation methods are available. The flavanoids or mixtures thereof are useful in pharmaceutical contexts where alopecia is caused by chemotherapy or radiation treatment, and in cosmetic contexts where the stimulation is intended to correct, for example, male pattern baldness, receding hairlines, or provide for more luxuriant hair growth.

Thus, in one aspect, the invention is directed to a method to stimulate the growth of hair in an area on the surface of a subject which method comprises providing said area with at least one isolated flavanoid derived from *Ginkgo biloba* or with an extract of *Ginkgo biloba* enriched in said flavanoids.

In other aspects, the invention is directed to pharmaceutical compositions that include, as active ingredients, at least one isolated flavanoid or which include an extract of *Ginkgo biloba* leaves enriched in flavanoids. In still other aspects, the invention is directed to cosmetic compositions which comprise at least one isolated flavanoid or an extract of *Ginkgo biloba* enriched in flavanoids.

In still other aspects, the invention is directed to methods of treating male pattern baldness, encouraging luxuriant growth of facial or coiffure-related hair or correcting receding hairlines using the flavanoid compositions of the invention. In still other aspects, the invention is directed to remedying the alopecia side effects of medication or radiation using these flavanoid-based materials.

BRIEF DESCRIPTION OF THE DRAWINGS

FIG. 2A shows the results when 20S proteasomes are treated directly; FIG. 2B shows the results when red blood cells are treated with these compounds.

MODES FOR CARRYING OUT THE INVENTION

Figure 1:
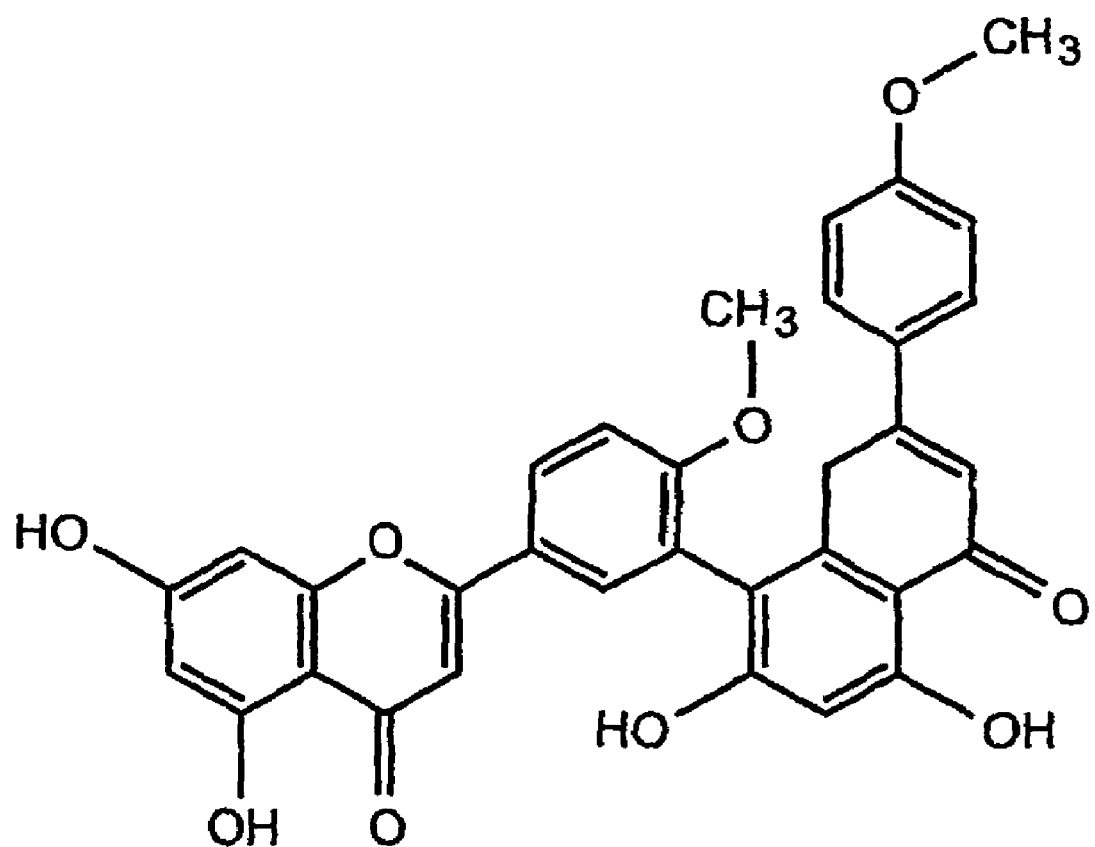
FIG. 1 shows the structure of isoginkgetin.

The importance of stimulating hair growth can arise in a large number of contexts. Of perhaps the most acute importance is the desirability of negating the alopecia that occurs as a side effect in cancer patients treated using chemotherapy and/or radiation. In addition to the severe discomfort of such treatments, combined with the uncertainties related to efficacy, the patient is subjected to the added trauma of hair loss and attendant effects on self-image. These effects can feed back physiologically onto the success or lack thereof of the treatments and it is thus of both medical and humanitarian significance to correct this condition. The materials provided in the present invention can ameliorate at least this negative dimension of treatment.

Of less acute concern, but nevertheless troublesome to the subjects involved, is hair loss due to aging or inborn abnormality. The angst associated with male pattern baldness is well known; alternative patterns of hair loss, such as receding hair lines, are equally troubling to the individuals involved. In addition, the quality of head hair in both men and women often deteriorates with age, resulting in thinning and inability to be manipulated into an attractive coiffure. The present invention provides a means to restore the luxuriance of head hair, thus adding to the quality of life of the individual.

While it may be possible to apply the materials and compositions of the invention systemically, clearly it is preferable to apply them topically directly to the area to be affected. Accordingly, preferred formulations for both pharmaceutical and cosmetic use will employ excipients that are suitable for topical application. Topical formulations typically are gels, salves, powders, or liquids, though controlled formulations which release defined amounts of active ingredient at the desired surface are also desirable. The formulations may contain materials which enhance the permeability of the active moieties through the epidermis. Such penetrants include, for example, DMSO, various bile salts, non-toxic surfactants and the like. Standard ingredients for cosmetic/pharmaceutical compositions are well known in the art; formulations for topical application of pharmaceuticals are found in *Remington's Pharmaceutical Sciences*, latest edition, Mack Publishing Co., Easton, Pa., incorporated herein by reference. Cosmetic formulations are widely varied and well known to practitioners.

A particularly advantageous formulation involves the use of liposomes which appear to direct their contents specifically to hair follicles. Such compositions are described, for example, in U.S. Pat. Nos. 5,965,157 and 6,261,596, both incorporated herein by reference.

Thus, the application includes compositions for topical use of the active ingredients whether for strictly cosmetic or pharmaceutical/cosmetic purposes. Individuals who are able to take advantage of the compositions and materials of the invention include patients undergoing radiation and/or chemotherapeutic treatments, men whose hairline is receding or who are experiencing pattern baldness, men whose beard growth is not adequate for their tastes, women whose head hair is thinning, and, in short, any individual desiring more hair growth in a particular region of his or her bodily surface. While the primary use of the materials of the invention is intended for humans, there may be instances where hair growth is desired on domestic or farm animals or in experimental animals.

Indeed, one aspect of the invention is the use of experimental animals to confirm the safety and efficacy of the compositions of the invention. Thus, products intended for use in humans may be applied to laboratory animals such as rats, mice or rabbits to confirm the ability of the individual preparation to stimulate hair growth and to assure that an individual preparation is not toxic. The use of the materials of the invention in the context of quality control, as just described, is part of the invention.

The active ingredient in the compositions of the invention may be an isolated flavanoid which is derivable from *Ginkgo biloba*. The isolated flavanoid molecule may be essentially pure—e.g., 90-100% pure or 90-99% pure or about 95% pure and may be actually isolated from *Ginkgo* leaves, or may be synthesized using standard organic chemistry techniques. The structures of flavanoids contained in *Ginkgo* leaves has been elucidated as set forth above. The structure of isoginkgetin is shown in FIG. 1 as an illustrative example. Such structures may further be coupled with one or more sugars.

Thus, the "isolated flavanoid" is an individual compound that is essentially pure and that corresponds to a compound found in *Ginkgo* leaves, however that compound is prepared.

As noted, an individual isolated flavanoid may be the only active ingredient in the compositions of the invention or the isolated flavanoid may be mixed with other active ingredients, including additional flavanoid compounds, some of which may be those which correspond to flavanoids that exist in *Ginkgo* leaves.

As defined in the present application, a flavanoid "derived from *Ginkgo biloba*" refers to a flavanoid which is found either in glycosylated or non-glycosylated form in the leaves of this plant. Thus, "derived from" refers to such compounds whether they are actually prepared from the leaves or whether they are prepared synthetically.

Alternatively, the active ingredient may constitute an extract of *Ginkgo* leaves which has been enriched in flavanoid content. As noted above, the commonly used extract, typically prepared by extracting in 70% ethanol is designated EGb761 and contains 24% of flavone glycosides on a wt/wt basis. Enriched extracts will contain higher percentages of flavanoids (wt/wt), preferably at least 30% flavanoids, more preferably at least 40% flavanoids, more preferably at least 50% flavanoids, and most preferably at least 60% or 70% flavanoids.

As shown hereinbelow, the ability of the flavanoid fraction of *Ginkgo* leaves to stimulate hair growth is verified both directly and by the ability of these compounds to inhibit the activity of proteasomes. The nexus between proteasome inhibition and hair growth stimulation has already been established in U.S. Pat. No. 6,410,512 referenced above and incorporated herein by reference. Thus, the following examples demonstrate that the model *Ginkgo* flavanoid isoginkgetin is effective in stimulating hair growth.

The following examples are intended to illustrate but not to limit the invention.

Example 1

Proteasome Inhibition by Isoginkgetin

Proteasomes are prepared from either white blood cells (WBC), red blood cells (RBC), or packed whole blood (PWB). For preparation of white blood cells, 1 ml blood in heparinized microtainer tubes is diluted 1:1 (v/v) with saline, and layered over 1 ml NycoPrep™ separation medium. The preparation is centrifuged at 500×g (Sorvall RT 6000D, rotor H-1000B at 1500 rpm) for 30 min at room temperature. The WBC are recovered as the supernatant, washed with 3 ml PBS, and centrifuged at 500×g (Sorvall RT 6000D, rotor H-1000B at 1500 rpm) for 5 min at room temperature. After removal of supernatant, the WBC pellet is resuspended in 1 ml PBS and microcentrifuged at 6600×g (Eppendorf 5415C at 7000 rpm) for 10 min at room temperature. The supernatant is then removed and the WBC pellet frozen at −70° C. prior to proteasome analysis.

If RBC are used, the RBC pellet obtained in the process of obtaining WBC described above is recovered and washed with 3 ml PBS, then centrifuged at 500×g (Sorvall RT 6000D, rotor H-1000B at 1500 rpm) for 5 min at room temperature. The supernatant is removed and the RBC pellet resuspended in 1 ml PBS and microcentrifuged at 6600×g (Eppendorf 5415C at 7000 rpm) for 10 min at room temperature. The supernatant is again removed and the RBC pellet is then frozen at −70° C. prior to proteasome analysis.

If packed whole blood is used as a source for proteasomes, 1 ml blood collected in heparinized microtainer tubes is diluted 1:1 (v/v) with saline and centrifuged at 500×g (Sorvall RT 6000D, rotor H-1000B at 1500 rpm) for 5 min at room temperature. The supernatant is removed and the PWB pellet resuspended in 1 ml PBS and microcentrifuged at 6600×g (Eppendorf 5415C at 7000 rpm) for 10 min at room temperature. The supernatant is removed and the PWB pellet is then frozen at −70° C. prior to proteasome analysis.

To prepare the proteasomes, WBC or RBC or PWB 1:1 (v/v) are lysed using 5 mM EDTA, pH 8.0 for 30 min and centrifuged at 15,000×g (Eppendorf 5415C at 14,000 rpm) for 10 min at room temperature. The supernatant containing proteasomes is placed on ice and the protein concentration is determined.

As a control, serial dilutions of a known proteasome inhibitor, in this instance Proteasome Inhibitor I (PSI or OSA) or lactacystin are prepared. Serial dilutions are also prepared of the compound to be tested. The reactions are then set up in 0.65 ml microfuge tubes to which are added 50 µl of the diluted samples and 2.0 µl of 0.5 µg/ml 20S proteasome, as described below. The tubes are incubated for 1 hr at 37° C. and placed on ice for assay within 6 hrs.

For the assay, 50 µl sample—i.e., 20 proteasome; or standard; or ~50 µg/µl WBC; or ~500 µg/µl RBC or ~1000 µg/µl PWB samples some containing test compounds is added to 50 µl substrate buffer (20 mM HEPES, 0.5 mM EDTA, 0.05% SDS, and 120 µM LLVY-AMC; pH 8.0) in a 96-well black fluorescence plate. The reaction is measured with a fluorescence spectrophotometer (excitation max.: 380 nm; emission max.: 440 nm, and velocity of reaction determined. As shown, the substrate is Leu-Leu-Val-Tyr-AMC. AMC is amido-4-methylcoumarin.

Figure 2A:
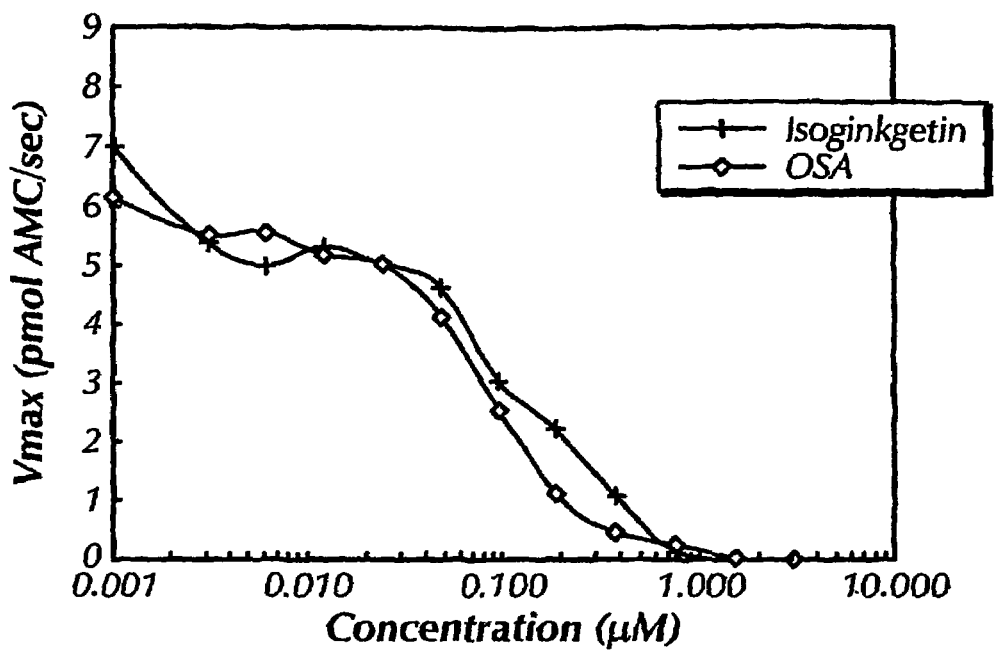
FIGS. 2A and 2B show, graphically, the results of a proteasome inhibition assay in the presence of isoginkgetin and of OSA.
Figure 2B:
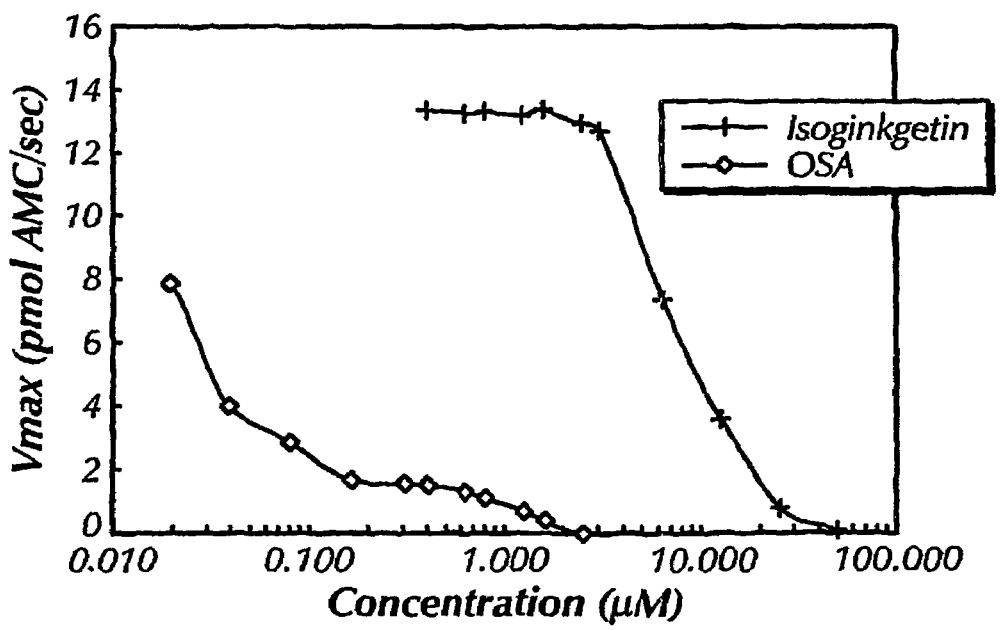

The results are shown in FIGS. 2A and 2B. The results in FIG. 2A were obtained using 20S proteasome preparations from packed whole blood of mice wherein the OSA and isoginkgetin were added directly to the proteasome preparation. As shown in FIG. 2A, both OSA and isoginkgetin similarly inhibit the Vmax of the proteolytic cleavage of the LLVY-AMC substrate. As shown in FIG. 2B, the inhibition by OSA is more effective when red blood cells are treated with these compounds in view of the greater ability of OSA to permeate the cells. It will be recalled that in these assays, the red blood cells are first treated with the compounds and then the proteasomes isolated for assessment of their protease activity.

Example 2

Stimulation of Hair Growth

C57 male black mice, 8 weeks old, were acclimated for 7 days in individual cages and fed standard diets and water ad libitum. The mice were anesthetized prior to manipulation. The dorsal trunk of each mouse was shaved and then treated topically starting the following day with a 1.0% solution of OSA (100 µl) which was applied for each of 5 days. A similar protocol was followed using 50 µl solution of isoginkgetin at percentages of 1, 5 and 10% wt/wt. The progression of hair growth is monitored visually and photographed.

Figure 3A:
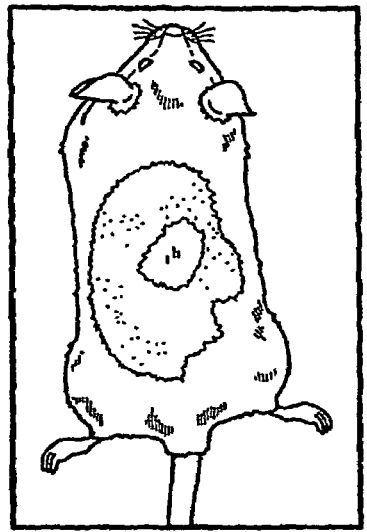
FIGS. 3A and 3B show the comparative affect of 1% OSA and 10% isoginkgetin on hair growth after 17 and 26 days, respectively.
Figure 3A:
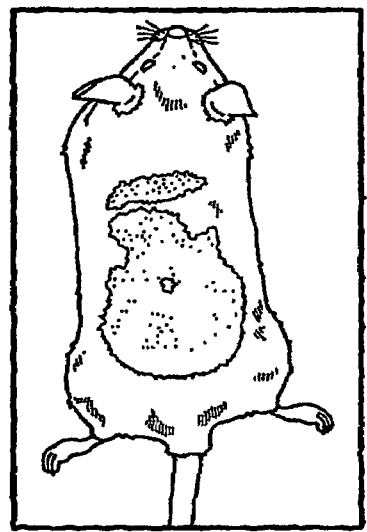
Figure 3A:
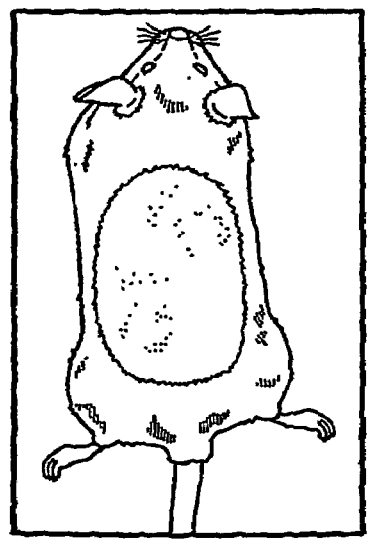
Figure 3B:

FIGS. 3A and 3B show the results for 1% OSA or 10% isoginkgetin after 17 days and 26 days respectively. As shown, both OSA and isoginkgetin stimulate the growth of hair in the dorsal area as compared to control.

The invention claimed is:

1. A method to stimulate the growth of hair in an area on the surface of a hair-bearing subject, which method comprises administering to said area a composition that comprises isolated and purified isoginkgetin.

2. The method of claim 1 wherein the subject is afflicted with male pattern baldness.

3. The method of claim 1 wherein said surface comprises facial or coiffure related hair.

4. The method of claim 1 wherein said subject is afflicted with alopecia caused by radiation or chemotherapy.

5. The method of claim 1 wherein said administering is by topical application.

* * * * *